US008453648B2

(12) United States Patent
Black et al.

(10) Patent No.: US 8,453,648 B2
(45) Date of Patent: Jun. 4, 2013

(54) ENDOTRACHEAL TUBE WITH INTRINSIC SUCTION AND ENDOTRACHEAL SUCTION CONTROL VALVE

(76) Inventors: Paul William Black, Highlands, NC (US); Lelia Meadows Martin, Highlands, NC (US)

( * ) Notice: Subject to any disclaimer, the term of this patent is extended or adjusted under 35 U.S.C. 154(b) by 95 days.

(21) Appl. No.: 13/155,381

(22) Filed: Jun. 7, 2011

(65) Prior Publication Data
US 2011/0237896 A1 Sep. 29, 2011

Related U.S. Application Data

(63) Continuation-in-part of application No. 11/855,995, filed on Sep. 14, 2007, now abandoned.

(51) Int. Cl.
*A62B 9/02* (2006.01)
(52) U.S. Cl.
USPC ........................................ 128/205.24; 604/35

(58) Field of Classification Search
USPC .................. 604/33, 35, 96.01, 129, 540, 541; 128/200.24, 200.26, 202.27, 205.24, 207.14–207.16; 137/528, 532, 533.17, 534, 137/538; 251/187, 190, 205, 213, 226, 227, 251/324, 337
See application file for complete search history.

*Primary Examiner* — Melanie Hand (57) ABSTRACT

An improved endotracheal tube providing a built in suction channel for the removal of excessive secretions from the lumen of said tube and the tracheobronchial system is disclosed. Control valves for regulating the suction feature are also disclosed. In at least one embodiment, the endotracheal tube includes an additional suction channel, an above-the-cuff suction channel adapted to remove secretions above the cuff outside the endotracheal tube and within the trachea. Additionally, in at least one embodiment, the endotracheal tube is configured for use with an endoscope for videolaryngoscopy, and the like. Furthermore, in at least one embodiment, an improved technology for the administration of medications within the tracheobronchial system is disclosed.

23 Claims, 11 Drawing Sheets

ENDOTRACHEAL TUBE WITH INTRINSIC SUCTION AND ENDOTRACHEAL SUCTION CONTROL VALVE

CROSS-REFERENCE TO RELATED APPLICATION(S)

This present non-provisional patent application is a continuation-in-part of copending U.S. patent application Ser. No. 11/855,995 filed on Sep. 14, 2007, and entitled "ENDOTRACHEAL TUBE WITH INTRINSIC SUCTION & ENDOTRACHEAL SUCTION CONTROL VALVE," and of which the application cited above is incorporated in-full by reference herein.

FIELD OF THE INVENTION

The technology described herein relates generally to endotracheal tubes used for intubating the trachea and like opening of human and animal bodies.

BACKGROUND OF THE INVENTION

During general anesthesia the gasses introduced through the endotracheal tube and the tube itself create irritation in the tracheobronchial system resulting in secretions that must be suction removed periodically by the anesthesiologist to clear the airway.

In the current conventional system, this requires detaching the gas delivery apparatus from the end of the endotracheal tube so a smaller suction tube can be introduced and passed down the lumen of the endotracheal tube. When the suctioning is finished, the gas delivery apparatus must be reattached. Thus, the flow of essential gasses to the patient is temporarily interrupted and some gasses undesirably escape into the operating room air breathed by the operating team, which can present a risk to the team personnel. Furthermore, the movement of the endotracheal tube and the insertion of yet another foreign object, the conventional suction tube itself, often stimulates involuntary patient muscle contractions and movements which can cause bleeding or otherwise interfere with surgical maneuvers.

BRIEF SUMMARY OF THE INVENTION

The technology described herein revises, modifies, improves, and extends the originally presented purpose, design, and function of the specialized endotracheal tube as disclosed in Applicants' application, U.S. patent application Ser. No. 11/855,995 filed on Sep. 14, 2007, and entitled "ENDOTRACHEAL TUBE WITH INTRINSIC SUCTION & ENDOTRACHEAL SUCTION CONTROL VALVE," and of which the application cited above is incorporated in-full by reference herein.

The improved specialized endotracheal tube further provides the capability to remove accumulated secretions above the cuff outside the endotracheal tube and within the trachea as well as within the tube and beyond in the tracheobronchial system as originally presented. This alteration also permits use with an endoscope and videolaryngoscopy to assist in insertion (intubation) through the vocal cords and accurate placement of the tube. This is of significant value in difficult cases. The new revisions also provide for ease of administration of intratracheobronchial medications. The suction and medication functions are accomplished with a closed system to reduce the possibility of contamination in the work area as well as infection in the patient (post intubation/anesthetic pneumonia) from the potentially contaminated secretions.

The intrinsic suction channel previously described is modified in shape, size and configuration to allow it to be used also as a conduit for a flexible endo scope with its tip optical lens positioned at or near the tip of the endotracheal tube. This allows for visualization per videolaryngoscopy to precisely insert the endotracheal tube between the vocal cords and place it at the desired distance within the trachea. After insertion of the endotracheal tube, the endoscope is removed. That same channel then is used for suction removal of secretions within the endotracheal tube and beyond the end of the tube from the tracheobronchial system. The same channel is used for direct administration of medications into the trachea and beyond. This modified intrinsic suction channel has also a redesign of the suction holes between its channel and the main lumen inside the endotracheal tube and at its tip. These holes open on the sides of the rounded suction channel to more effectively attack the secretions which accumulate within the tube, and the revised opening at the tip better attacks those secretions in the tracheobronchial system.

In addition, a new separate second suction channel, the above the cuff suction channel, is designed to remove secretions pooling above the cuff within the trachea but outside the endotracheal tube. Therefore its suction holes present to the outside of the endotracheal tube just above the cuff.

Suction is applied to either one or the other of the two suction channels individually by way of an integral suction select valve which directs the suction function into the selected channel when the suction is activated as originally presented via the suction control valve connected to the suction source. These suction functions are accomplished with a closed system so that it is not necessary to uncouple/disconnect the gas delivery system from the endotracheal tube or the suction source from the suction channels. Therefore, contamination of the area is minimized relative to the systems in common usage which require uncoupling and introduction and withdrawal of separate suction tubes in order to clear secretions.

The introduction and administration of medications into the tracheobronchial system is also effected by way of the intrinsic suction channel, and again uncoupling/disconnecting the gas delivery system or the suction source is not required.

The same benefit is realized relative to minimization of contamination compared to the method in common usage where uncoupling is required.

This specialized endotracheal intubation system as originally presented including the Suction Control Valve and now as revised is adapted to serve all the major needs of gas administration and airway management in a clean fashion: endoscopic videolaryngoscopy, gas delivery, removal of potentially contaminated secretions, administration of medications, and maintenance of as clean an environment as possible for the patient and for the work area and the personnel in attendance.

In an exemplary embodiment of the technology described herein, an endotracheal tube with intrinsic suction and above-the-cuff suction. The endotracheal tube includes: an outer tube, the outer tube having a proximal end, a distal end, and a lumen, wherein the outer tube approximates an inner diameter of a body passage to be intubated; an inflatable cuff, encircling the outer tube near the distal end, and adapted to provide a seal; an intrinsic suction channel integrally formed within the lumen of the outer tube, the intrinsic suction channel spanning from above the proximal end to the distal end of the outer tube and having an opening at the distal end and a plurality of openings along a length of the intrinsic suction channel, the intrinsic suction channel configured to allow a plurality of fluids to be suctioned into the intrinsic suction channel from an area surrounding the distal end of the outer tube and from an area within the lumen of the outer tube; and an above-the-cuff suction channel integrally formed within the lumen of the outer tube, the above-the-cuff suction channel spanning from above the proximal end of the outer tube to immediately above the cuff and having a plurality of holes disposed immediately above the cuff and which open from the above-the-cuff suction channel to an outside of the outer tube at the above-the-cuff suction channel farthest distal extent and adapted to remove secretions which accumulate above the cuff within the trachea and outside of the outer tube.

The endotracheal tube also can include a suction select valve configured for operable selection between a first suction action in the intrinsic suction channel to remove secretions within the outer tube and beyond from the tracheobronchial system and a second suction action in the above-the-cuff suction channel to remove secretions above the cuff outside the outer tube and within the trachea.

The endotracheal tube further can include an endoscopy and medicine port configured for operable insertion of an endo scope and a medicine, wherein the endoscopy and medicine port is fluidly coupled to the intrinsic suction channel. The endoscopy and medicine port is adapted to directly administer medications into the tracheobronchial system without the need to uncouple and disconnect a gas delivery system and a suction system. The endoscopy and medicine port is adapted to receive the insertion of a flexible endoscope for videolaryngoscopy to assist in accurate passage of the endotracheal tube between the vocal cords and proper positioning with the trachea.

The endotracheal tube also can include the intrinsic suction channel defined by a Y-branch extended side arm, wherein a first branch of the Y is adapted for the suction select valve, and wherein a second branch of the Y is adapted for the endoscopy and medicine port.

The endotracheal tube further can include an extension tube having an opening defined at its terminus, fluidly coupled to the intrinsic suction channel and the above-the-cuff suction channel of the endotracheal tube and outwardly extending from generally the proximal end of the outer tube, to provide a removal path out of the body passage for the plurality of fluids suctioned into the intrinsic suction channel and the above-the-cuff suction channel. The suction select valve is disposed with the extension tube in at least one embodiment.

The endotracheal tube also can include: an end cap selectively placed on a proximal end of the extension tube to close the proximal end of the extension tube; and a security tether to connect the end cap to the extension tube; a locking plate extension having a locking plate opening defined in a margin of a body wall of the extension tube at the terminus and adjacent to the extension tube opening; and a cylindrical projection with a rounded tip defined with the end cap and adapted to securely couple to a tubular lumen of the extension tube when not in use.

In at least one embodiment, the intrinsic suction channel includes a round circumferential shape and the openings along the length of the intrinsic suction channel are alternated from a first side to a second side of the intrinsic suction channel and staggered in distribution.

The endotracheal tube also includes: an air passageway located within the wall of the outer tube and fluidly coupled to the inflatable cuff; an inflation extension tube fluidly coupled to the air passageway in the wall of the outer tube and outwardly extending from the proximal end of the outer tube; and a filler valve coupled to a proximal end of the inflation extension tube to regulate the flow of air entering or exiting the inflation extension tube and the inflatable cuff.

The endotracheal tube also can include a radiopaque strip located within the outer tube in a portion of the outer tube located underneath the suction channel and extending longitudinally from the distal end of the outer tube to the proximate end of the outer tube to disallow the passage of radiation.

The endotracheal tube further can include an opening in the outer tube located between a tip of the endotracheal tube and an inflatable cuff to assist in ventilation and help avoid complete endotracheal tube obstruction.

The suction select valve also can include: a valve housing; a Y-shaped tubular passageway fluidly coupled to the intrinsic suction channel and the above-the-cuff suction channel, wherein a first branch of the Y is adapted for the intrinsic suction channel and wherein a second branch of the Y is adapted for the above-the-cuff suction channel; and a cylindrical internal reciprocatable element adapted to rotate operably within the valve housing in a limited defined range between the first branch of the Y and the second branch of the Y, thereby between a first suction action in the intrinsic suction channel to remove secretions within the outer tube and beyond from the tracheobronchial system and a second suction action in the above-the-cuff suction channel to remove secretions above the cuff outside the outer tube and within the trachea.

In another exemplary embodiment of technology described herein, a method for intubating a patient with an endotracheal tube having intrinsic suction and above-the-cuff suction is disclosed. The method includes: providing the endotracheal tube as defined in the embodiments above, and further including: placing the endotracheal tube within the patient; selectively utilizing the intrinsic suction channel as necessary to remove secretions within the outer tube and beyond from the tracheobronchial system; and selectively utilizing the above-the-cuff suction channel as necessary to remove secretions above the cuff outside the outer tube and within the trachea.

The method also can include providing an endotracheal tube having a suction select valve as defined above, and operatively turning the suction select valve to select either the first suction action in the intrinsic suction channel or the second suction action in the above-the-cuff suction channel.

The method also can include providing an endotracheal tube having an endoscopy and medicine port as defined above, and directly administering a medicine into the tracheobronchial system without the need to uncouple and disconnect a gas delivery system and a suction system; and directly administering an insertion of a flexible endoscope for videolaryngoscopy to assist in accurate passage of the endotracheal tube between the vocal cords and proper positioning with the trachea.

The method also can include providing an endotracheal tube having an extension tube as defined above, and removing the plurality of fluids suctioned into the intrinsic suction channel and the above-the-cuff suction channel.

The method further can include providing an endotracheal tube having an end cap, security tether, locking plate extension, and cylindrical projection as defined above, and securely coupling the end cap to the tubular lumen of the extension tube when not in use.

The method also can include providing a suction select valve as defined above having a valve housing and a Y-shaped tubular passageway, and operatively selecting between the first suction action in the intrinsic suction channel and the second suction action in the above-the-cuff suction channel.

There has thus been outlined, rather broadly, the features of the present invention in order that the detailed description that follows may be better understood, and in order that the present contribution to the art may be better appreciated. There are additional features of the invention that will be described and which will form the subject matter of the claims. Additional aspects and advantages of the present invention will be apparent from the following detailed description of an exemplary embodiment which is illustrated in the accompanying drawings. The invention is capable of other embodiments and of being practiced and carried out in various ways. Also, it is to be understood that the phraseology and terminology employed are for the purpose of description and should not be regarded as limiting.

BRIEF DESCRIPTION OF THE DRAWINGS

The technology described herein will be better understood by reading the detailed description of the invention with reference to the accompanying drawing figures which are not to scale, in which like reference numerals denote similar structure and refer to like elements throughout, and in which.

DETAILED DESCRIPTION OF THE INVENTION

In describing the preferred and other embodiments of the technology described herein, as illustrated in FIGS. 1-10, specific terminology is employed for the sake of clarity. The invention, however, is not intended to be limited to the specific terminology so selected, and it is to be understood that each specific element includes all technical equivalents that operate in a similar manner to accomplish similar functions.

Figure 1:
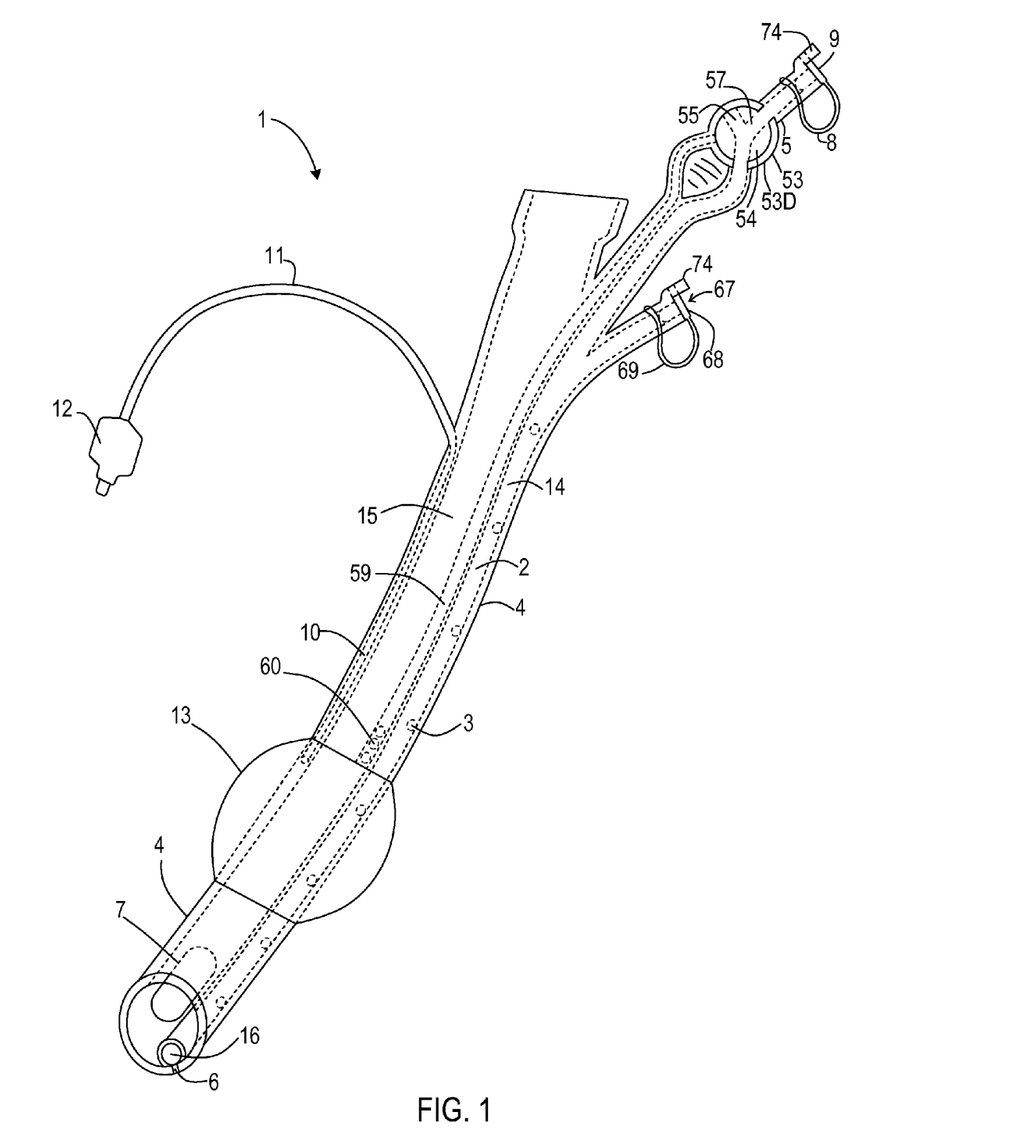
FIG. 1 is a perspective view of an improved endotracheal tube, according to an embodiment of the technology described herein; also

Referring now to FIG. 1 and FIGS. 2A, 2B, and 2C, illustrated therein is an embodiment of an improved endotracheal tube with intrinsic suction. An outer tube 4 has an outer diameter that approximates the inner diameter of the passage to be intubated. A built in intrinsic suction channel 2 runs through the outer tube 4. The intrinsic suction channel 2 is integrally formed within the lumen of the outer tube 4. The intrinsic suction channel 2 spans from above the proximal end to the distal end of the outer tube 4 and has an opening 16 at the distal end. The design configuration of the intrinsic suction channel 2 which courses along within the convex aspect of the endotracheal tube FIG. 1 is round. The intrinsic suction channel 2 extends beyond the main endotracheal tube past a new suction select valve 53 to become the suction extension tube 5 which, in use, is connected to one or the other of two versions of the suction control valve (FIGS. 4A through 8D) and then to the available Suction Source SS.

The intrinsic suction channel 2 includes a plurality of openings 3 along a length of the intrinsic suction channel 2 and allows the movement of fluids from the outer tube lumen 15 into the suction channel lumen 14. The intrinsic suction channel 2 is configured to allow a plurality of fluids to be suctioned into the intrinsic suction channel 2 from an area surrounding the distal end of the outer tube 4 through tip opening 16 and from an area within the lumen of the outer tube 4 by a plurality of holes 3. The plurality of holes 3 which permit fluid movement of secretions from the main outer endotracheal tube lumen 15 to the intrinsic suction channel lumen 14 are now placed along either side of the intrinsic suction channel 2 immediately adjacent to the contact point where the wall of the suction channel contacts/joins the inner aspect of the wall of the main endotracheal tube. The holes 3 may vary in number, size, shape, arrangement, position, distribution and location even though they are just along one side as depicted.

The endotracheal tube FIG. 1 includes an inflatable cuff 13, encircling the outer tube 4 near the distal end, and adapted to provide a seal. An air passageway 10 is located within the wall of the outer tube 4 and fluidly coupled to the inflatable cuff 13. An inflation extension tube 11 is fluidly coupled to the air passageway in the wall of the outer tube 4 and outwardly extending from near the proximal end of the outer tube 4. A filler valve 12 coupled to a proximal end of the inflation extension tube 11 to regulate the flow of air entering or exiting the inflation extension tube 11 and the inflatable cuff 13. The air passageway 10, filler valve 12 and inflation extension tube 11 allow air to be pumped into or out of the inflatable cuff 13.

The endotracheal tube FIG. 1 includes an above-the-cuff suction channel 59. The above-the-cuff suction channel AC, 59 is integrally formed within the lumen of the outer tube 4. The above-the-cuff suction channel 59 spans from above the proximal end of the outer tube 4 to immediately above the inflatable cuff 13. The above-the-cuff suction channel 59 has a plurality of holes 60 disposed immediately above the inflatable cuff 13 and which open from the above-the-cuff suction channel 59 to an outside of the outer tube 4 at the above-the-cuff suction channel farthest distal extent. The above-the-cuff suction channel 59 is adapted to remove secretions which accumulate above the cuff 13 within the trachea and outside of the outer tube 4.

The endotracheal tube FIG. 1 includes a suction select valve 53 configured for operable selection between a first suction action in the intrinsic suction channel 2 to remove secretions from within the lumen 15 of the outer tube 4 and beyond from the tracheobronchial system and a second suction action in the above-the-cuff suction channel 59 to remove secretions above the cuff 13 outside the outer tube 4 and within the trachea.

Figure 1A:
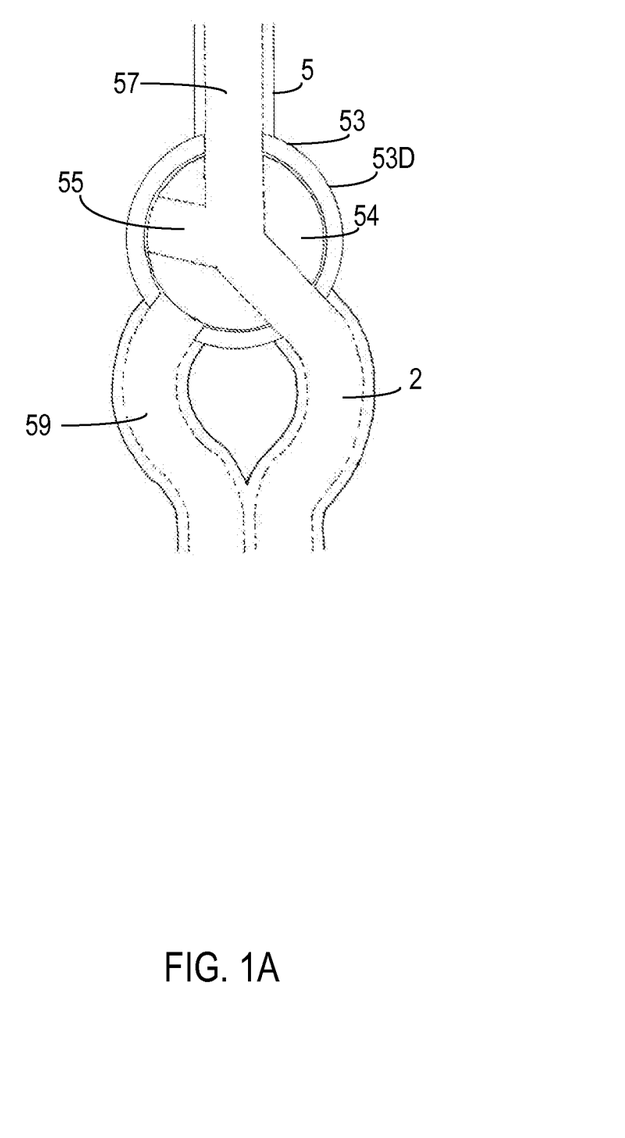
FIG. 1A is an enlarged perspective view of that portion of the improved endotracheal tube in FIG. 1 which depicts the integral suction select valve.
Figure 2A:
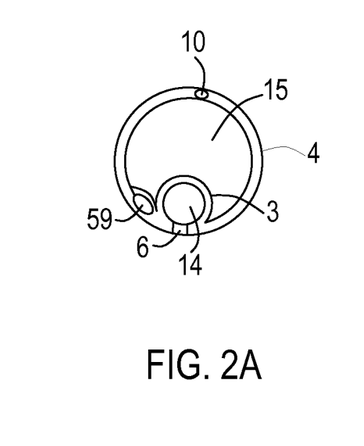
FIG. 2A and FIG. 2B are cross-sectional views of the endotracheal tube depicted in FIG. 1 above the cuff.
Figure 2B:
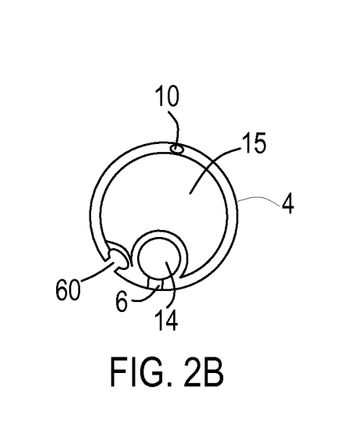
Figure 2C:
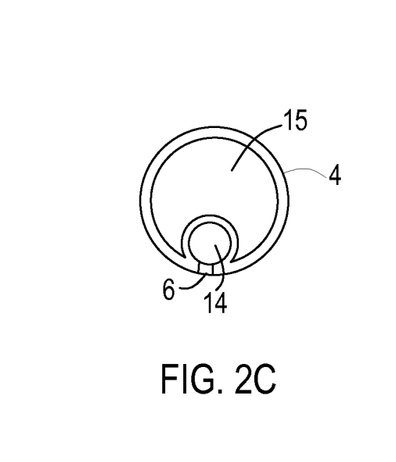
FIG. 2C is a cross sectional view depicted in FIG. 1 just below the cuff.

The new suction select valve 53 is depicted in frontal view 53B, side view 53A, and internal cut away views 53C, 53D. See FIG. 1, FIGS. 1A, 9A, 9B, and 9C. In FIG. 1 and FIG. 1A, 53D the suction select valve shows a cylindrical internal reciprocatable element 54 which rotates in a limited defined range and being snugly disposed within the lubricated outer housing of suction select valve 53. This element 54 is secured to the back of its housing by a center rotatable axle (not shown).

Within this reciprocatable element 54 is a Y-shaped tubular fluid passageway 55. When the reciprocatable element 54 is rotated to its full allowable defined range in one direction FIG. 1 and FIG. 1A, 57 it results in fluid alignment of its internal Y-shaped tubular passageway 55 allowing communication between the internal suction channel 2 and the suction extension tube FIG. 1 and FIG. 1A, 5 which is in turn connected to either one or the other of two versions of the suction control valve (the opening, activating or closing, deactivating device) depicted in FIGS. 4 through 8 and then to the suction source SS. Thus, when activated, suction is delivered to within the endotracheal tube via suction channel 2 and then via holes 3 as well as to the tip of the endotracheal tube and the tracheobronchial system via its suction channel end hole 16.

Figure 9A:
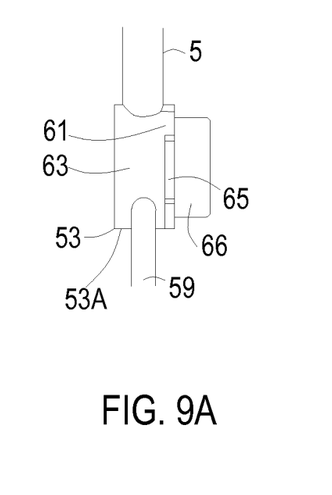
FIG. 9A is a side view of the suction select valve depicted in FIG. 1 and FIG. 1A.
Figure 9B:
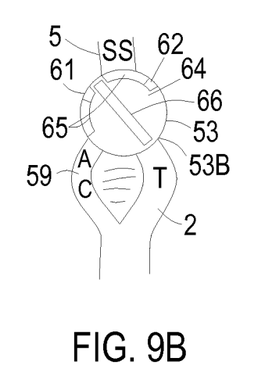
FIG. 9B is a front view of the suction select valve depicted in FIG. 1 and FIG. 1A.
Figure 9C:
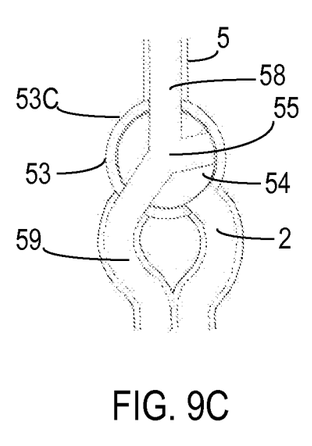
FIG. 9C is a cross-sectional enlarged view of the suction select valve depicted in FIG. 1 and FIG. 1A.
Figure 10A:
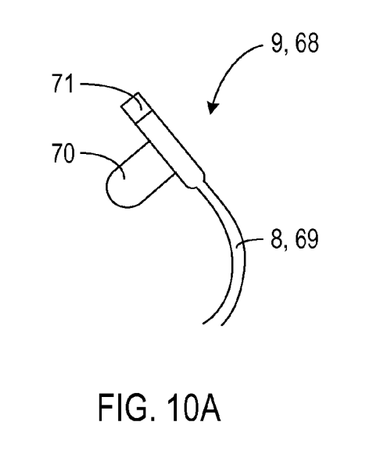
FIG. 10A is a side view of the end cap depicted in FIG. 1.
Figure 10B:
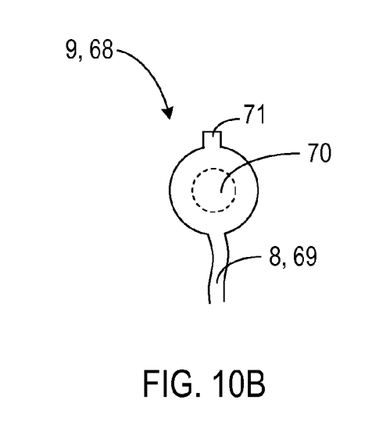
FIG. 10B is a top view of the end cap depicted in FIG. 1.
Figure 10C:
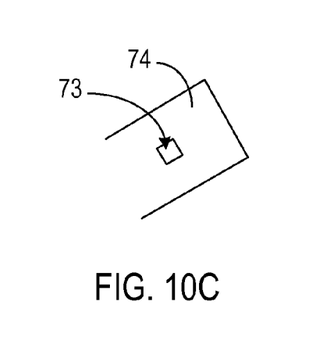
FIG. 10C is a front view of the end cap tab receiver depicted in FIG. 1.

When the rotatable element 54 within the suction select valve 53 is rotated in the opposite direction FIG. 9C, 58 to its defined limit it results in fluid alignment of the above-the-cuff suction channel 59 and the suction extension tube 5, etc. This permits suction removal of secretions pooling above the inflatable cuff 13 between the endotracheal tube and the tracheal wall via a plurality of holes 60 just above the cuff 13 and which open from the above-the-cuff suction channel 59 to the outside of the endotracheal tube at the channel's farthest distal extent. Three such holes 60 are depicted, but their number, size, shape, arrangement, position, distribution and location may vary.

As depicted specifically in FIGS. 9A, 9B, and 9C, the rotation of the reciprocatable cylindrical element 54 is limited and defined by stable fixed stop blocks 61, 62 which are simple extensions of the outer shell 63 housing the reciprocatable cylindrical element 54. When the element 54 rotates, the stop blocks 61, 62 abut and impinge on margins of lateral rim cut outs 65 of a flat front cover 64 which is fixed to the cylindrical rotational element 54. These cut outs 65 also permit the rotational excursion and, together with the stop blocks 61, 62 they also restrict and limit the range of the rotational excursion so that at each extreme of allowable rotation either the intrinsic suction channel 2 or the above-the-cuff suction channel 59 is selected for suction function.

The defined rotational movement is effected by a turn blade handle 66 projecting away from the face plate at 90 degrees and fused to the face plate. The blade 66 is positioned on the face plate such that when rotated it points at the specific suction channel selected, either 2 or above-the-cuff suction channel 59. For ease of selection, the external aspect of the intrinsic suction channel 2 is clearly marked with a T for trachea, and the above-the-cuff suction channel 59 is clearly marked externally with AC for above the cuff.

The suction extension tube 5 is depicted quite short, but it would be longer in reality. It is covered when not in use by a revised cap 9 and security tether 8. See FIGS. 1, 10A, 10B, and 10C. The cap 9 has on its underside a cylindrical projection with rounded tip 70 which inserts snugly into the tubular lumen of the suction extension tube 5 when it is not in use. The cap 9 is shown in place. The cap 9 also has a tongue like short projection 71 on its leading edge which effects a locking engagement into an opening 73 in a lock plate extension 74 from one margin of the body wall of the suction extension tube 5 at its terminus and adjacent to its opening.

The endotracheal tube FIG. 1 includes a Y branch extended side arm continuation of the intrinsic suction channel 2 which projects from the upper area and ends with an open port called the dedicated endoscopy and medicine port 67 (endoscopy/med port). This port is equipped with a cap 68 and tether 69 (like on the suction extension tube 9, 8) for secure closure when not in use.

The endoscopy/med port 67 enables the use of the revised conduit previously only known as the intrinsic suction channel 2 to be used to pass a flexible endo scope within it to or near its tip to permit videolaryngoscopic accurate placement of this multi-specialized endotracheal tube between the vocal cords and properly locate it in the trachea (intubation). After intubation, the endo scope is withdrawn. This novel feature is of tremendous value especially in cases of difficult intubation.

The same endoscopy/med port 67 is available after intubation for the direct administration of medications into the tracheobronchial passages without any need to disconnect either the gas delivery system to the endotracheal tube or the available suction source from the suction extension tube 5. Furthermore, the endoscopy/med port 67 is available also for other therapeutic modalities which may come into use in the future.

Figure 3:
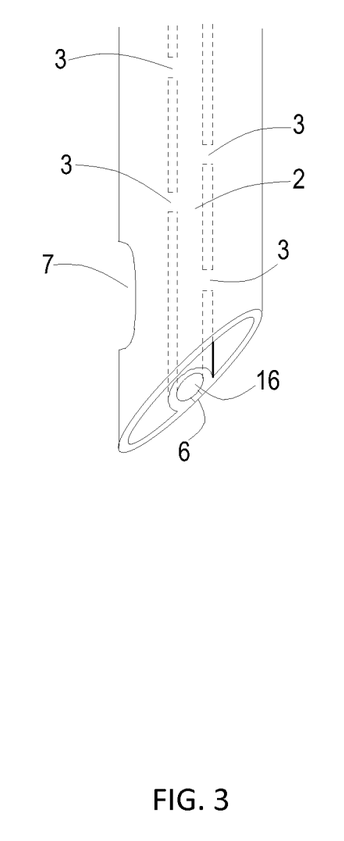
FIG. 3 is a side view (from the concave side) of the endotracheal tube depicted in FIG. 1 just below the cuff.

A side opening 7 is positioned near the end of the outer tube 4, FIGS. 1 and 3. The opening 7 is a "Murphy's Eye hole" disposed in the outer tube and located between a tip of the endotracheal tube and an inflatable cuff 13 to assist in ventilation and help avoid complete endotracheal tube obstruction.

A radiopaque strip 6 runs the length of the outer tube 4 underneath the suction channel 2. The radiopaque strip 6 extends extending longitudinally from the distal end of the outer tube 4 to the proximate end of the outer tube to disallow the passage of radiation.

Referring now to FIG. 3 which depicts the tip of the endotracheal tube below (distal to) the inflatable cuff 13 as viewed from the concave side of the tube and as revised in this addendum. The design and configuration and functionality are modified from the original disclosure. The intrinsic suction channel 2 is changed from elliptical to round in circumferential shape as depicted at its tip opening 16. Also the holes 3 depicted at the sides of the round intrinsic suction channel 2 are depicted at the sides alternately on one side and then the other and staggered in distribution. It has been noted previously that these holes 3 may vary in number, size, shape, arrangement, position, distribution and location. While it is not shown specifically, the cuff is located well away from the tip of the tube (typically approximately 3 centimeters in an adult size tube).

Figure 4A:
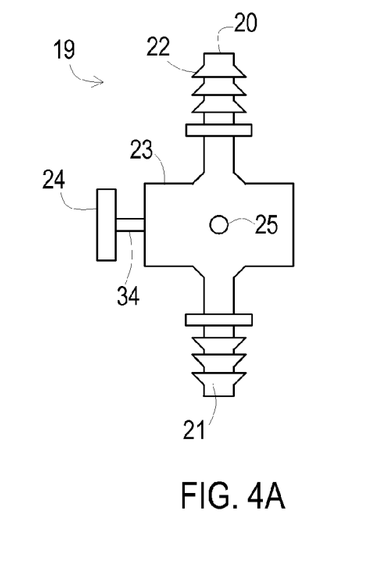
FIG. 4A is a front view of the first of two versions of the suction control valve means.

Referring now to FIG. 4A, illustrated therein is a front view of the first version of the suction control valve means 19 for the regulation of the flow of fluids through the suction channel 2 or the above-the-cuff suction channel AC, 59 depending on which suction function is selected by the suction selection valve 53. A fluid outlet port 20 and a fluid inlet port 21 extend outwards from the valve body 23. A hose connected to a suction system commonly found in operating environments will slide over the outlet port 20. The extension tube 5 of the endotracheal tube's FIG. 1 continuation of suction channel 2 and suction channel AC, 59 will slide over the inlet port 21. A plurality of ridges 22 on the outlet and inlet ports creates an airtight seal between the hoses and the ports. A vent hole 25 in the front of the valve body allows air from the surrounding room to be sucked into the suction system when the valve is in the closed position. An additional vent hole (not shown in this drawing) is also on the back side of the valve body. A push button 24 controls the operation of the valve. A stem 34 connects the push button to a sliding element within the valve body 23.

Figure 4B:
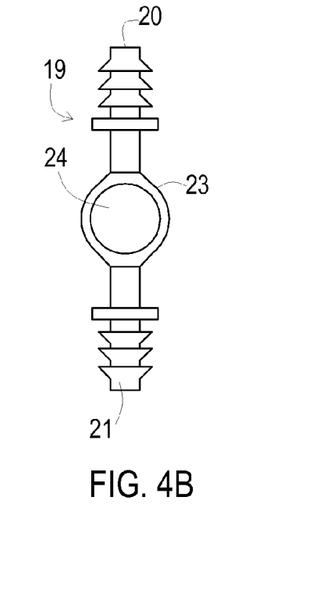
FIG. 4B and FIG. 4C are side views of the first valve means.

FIG. 4B shows a side view of the first version of the suction control valve means 19 from the side facing the push button 24.

Figure 4C:
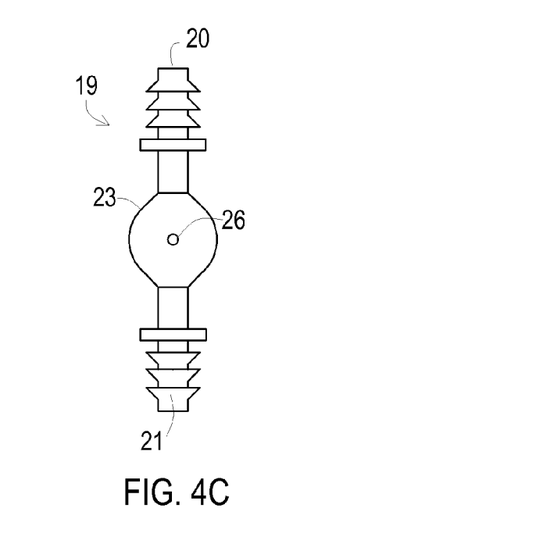

FIG. 4C shows another side view of the first version of the suction control valve means 19 from the side opposite the push button. A vent hole 26 allows air to move in and out of the valve body 23. This allows a reciprocatable element within the valve body to slide back and forth without creating a vacuum that could restrict the movement of the element.

Figure 5A:
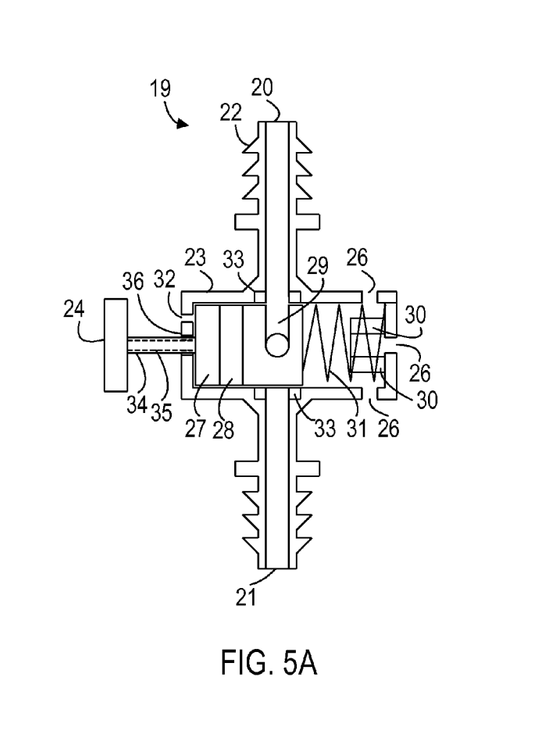
FIG. 5A is a front cross-sectional view of the first of two versions of the suction control valve means in its closed position.

FIG. 5A illustrates a cross-sectional view of the first version of the suction control valve means 19 showing the reciprocatable element 27 in its closed position. Two fluid passageways are disposed within the reciprocatable element 27. A suction passageway 28 has one opening at the bottom of the reciprocatable element 27 and one opening at the top. A suction bypass passageway 29 has one opening at the top of the reciprocatable element 27 and two openings on the sides of the reciprocatable element 27. A coil spring 31 keeps the valve in the closed position until an operator depresses the push button 24. Silicone washers 33 provide airtight seals between the reciprocatable element 27 and both the inlet port 21 and the outlet port 20. A plurality of vent holes 26 on the side of the valve body 23 opposite the push button and a vent hole 32 on the other side of the valve body (or end plate under the push button) allow air to move into and out of the space between the reciprocatable element 27 and the valve body 23 preventing a vacuum from forming that could restrict the movement of the reciprocatable element 27. Grooves 35 in the stem 34 align with ridges 36 in the hole in the end plate through which the push button stem slides. The engagement of the grooves and ridges keep the stem 34 and reciprocatable element 27 from rotating out of alignment. A bumper block 30 prevents the reciprocatable element 27 from being pushed beyond the open position. The bumper block 30 is shaped like a flat doughnut with a hole in the middle of it to allow air to pass through it and in and out of vent hole 26.

Figure 5B:
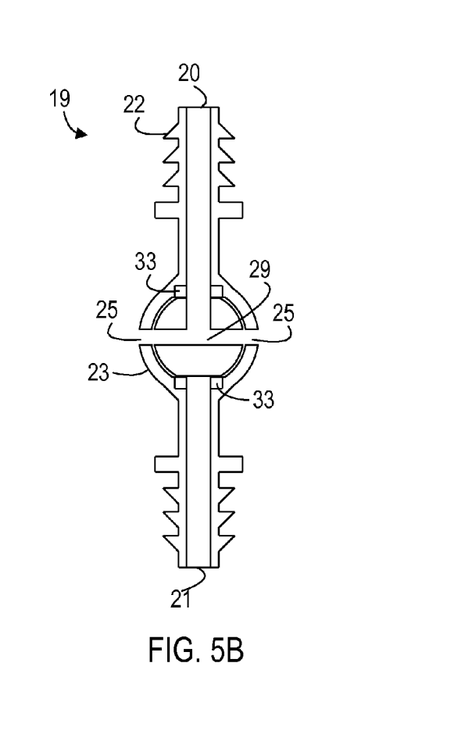
FIG. 5B is a side cross-sectional view of the first of two versions of the suction control valve means in its closed position.

FIG. 5B illustrates a side mid-cross-sectional view of the first version of the suction control valve means 19 in its closed deactivated position. The suction bypass passageway 29 is in fluid communication with the outlet port 20 and the two side vent holes 25 on each side of the valve body 23 allowing only room air to be suctioned.

Figure 5C:
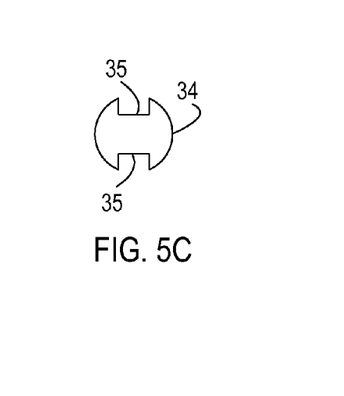
FIG. 5C is a cross-sectional view of the stem component of the first of two versions of the suction control valve means.

FIG. 5C illustrates a mid-cross-sectional view of the stem 34 connecting the push button with the reciprocatable element. Grooves 35 in the stem 34 align with opposing ridges attached to the valve body opening 36 in the body 23 end plate through which the stem slides back and forth.

Figure 6A:
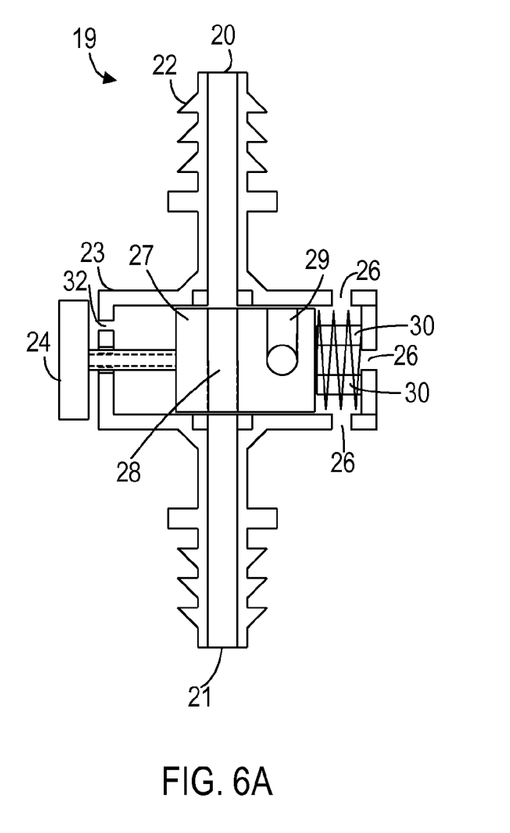
FIG. 6A is a front cross-sectional view of the first of two versions of the suction control valve means in its open position.

FIG. 6A illustrates a front cross-sectional view of the first version of the suction control valve means 19 with the push button depressed and the reciprocatable element 27 in its open activated position. In this position the suction passageway 28 is in fluid communication with the inlet port 21 and the outlet port 20 and the suction feature is functional. The push button 24 stops short of touching the control valve body by blocking action of bumper block 30 so as not to occlude vent hole 32.

Figure 6B:
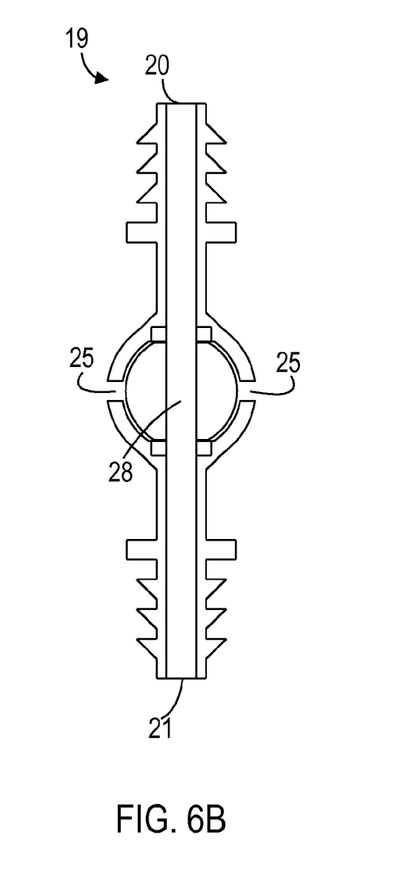
FIG. 6B is a side cross-sectional view of the first of two versions of the suction control valve means in its open position.

FIG. 6B illustrates a side mid-cross-sectional view of the valve means 19 in its open activated position.

Figure 7A:
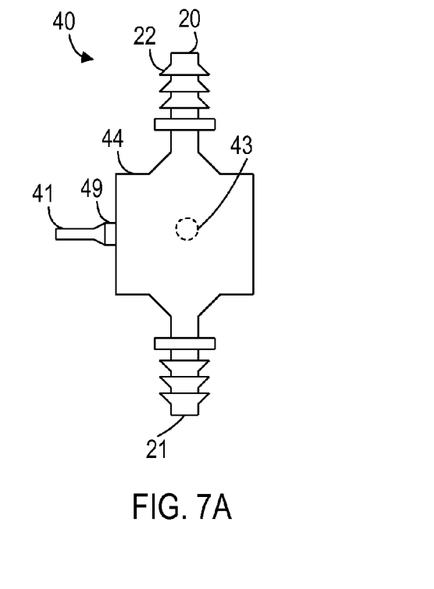
FIG. 7A is a front view of the second of two versions of the suction control valve means in its closed position.

FIG. 7A illustrates a front view of a second version of the suction control valve means 40 in its closed deactivated position. This valve utilizes a rotatable blade type knob 41 to turn a rotatable element disposed within the valve body 44. A round knob stem 49 connects the rotatable knob 41 to the rotatable element. An inlet port 21 and an outlet port 20 extend outward from the valve body 44. A vent hole 43 represented in this drawing as a dotted line is positioned on the back of the valve body 44.

Figure 7B:
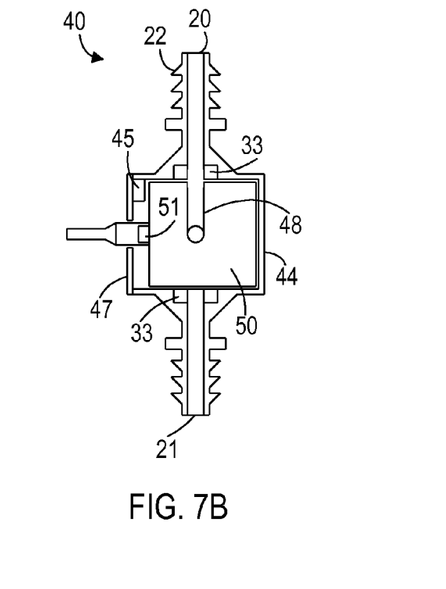
FIG. 7B is a front cross-sectional view of the second version of the suction control valve means in its closed position.

FIG. 7B illustrates a cross-sectional view of the second version of the suction control valve means 40 in its closed deactivated position exposing a rotatable element 50. A fluid passageway 48 is disposed within the rotatable element 50. A spring anchor block 45 is attached to the valve body 44 and a spring attachment post 51 is attached to the rotatable element 50. A spring not shown in this figure connects the anchor block 45 and attachment post 51 and keeps the rotatable element 50 in its closed position when the suction feature is not needed. A stop block (not shown in this figure) attached to the valve body keeps the attachment post 51 and rotatable element 50 from moving beyond the valves closed position and within the ninety degree rotation arc. The spring anchor block 45 and the stop block also serve as spacers between the end of the rotatable element and the body end plate 47 which encloses the inner components of the valve 40.

Figure 7C:
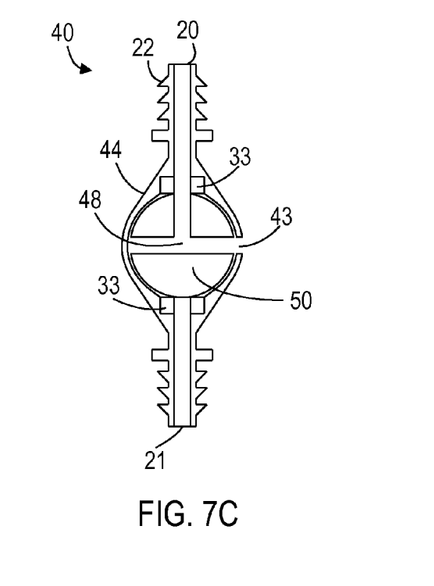
FIG. 7C is a mid side cross-sectional view of the second version of the suction control valve means in its closed position.

FIG. 7C illustrates a side mid-cross-sectional view of the second version of the suction control valve means 40 in its closed deactivated position. This view illustrates that the fluid passageway 48 is comprised of two separate passageways joined together and has three openings. In this closed position one opening is in fluid communication with the outlet port 20 and another one is in fluid communication with the back vent hole 43 so only room air is suctioned. A silicone washer 33 forms an airtight seal between the rotatable element 50 and the outlet port 20.

Figure 7D:
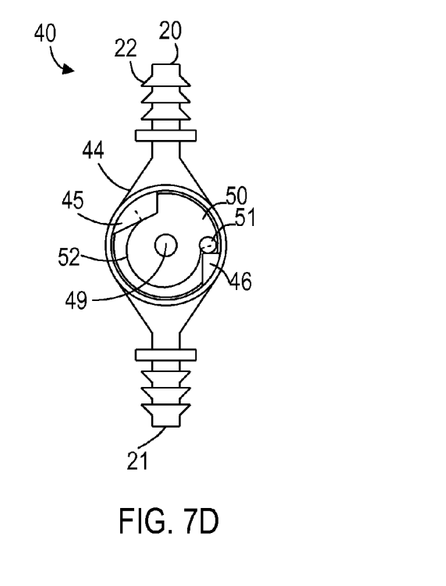
FIG. 7D is an end side cross-sectional view of the second version of the suction control valve means in its closed position.

FIG. 7D illustrates a side view of the second version of the suction control valve means 40 in the deactivated position without the endplate and the knob. A single leaf compression load type spring 52 is attached to the spring anchor block 45 and to the spring attachment post 51. A stop block 46 keeps the attachment post 51 and the rotatable element 50 from moving beyond the valve's closed position so only room air would be suctioned.

Figure 8A:
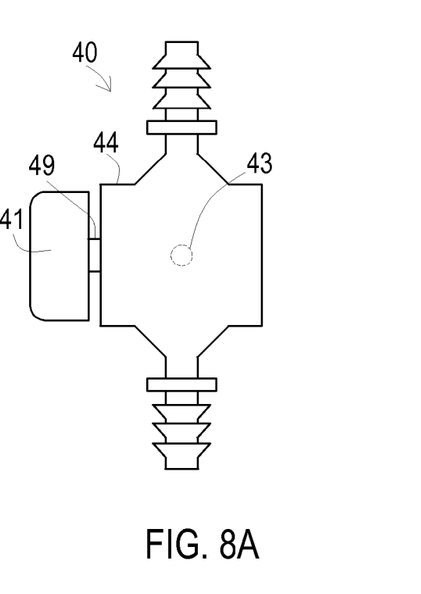
FIG. 8A is a front view of the second version of the suction control valve means in its open position.

FIG. 8A illustrates a front view of the second version of the suction control valve means 40 shown in FIG. 7A where its knob 41 has been rotated ninety degrees from its closed position into its open activated position.

Figure 8B:
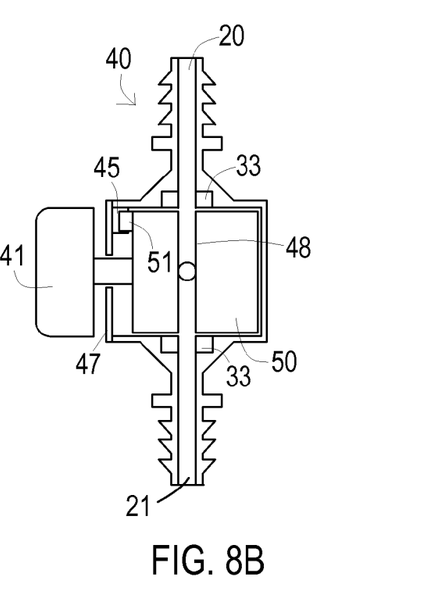
FIG. 8B is a front cross-sectional view of the second version of the suction control valve means in its open position.

FIG. 8B illustrates a front cross-sectional view of the second version of the suction control valve means 40 shown in FIG. 8A where the rotatable element 50 and knob 41 have been rotated ninety degrees into in its open activated position. In this position one of the openings of the fluid passageway 48 is in fluid communication with the outlet port 20 and one of the openings is in fluid communication with the inlet port 21 so the suction feature is functional.

Figure 8C:
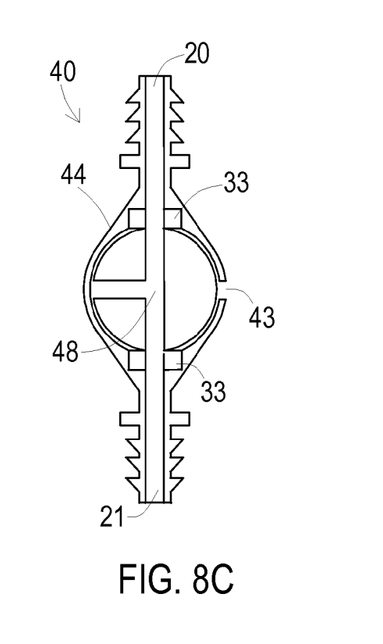
FIG. 8C is a mid side cross-sectional view of the second version of the suction control valve means in its open position.

FIG. 8C illustrates a side mid-cross-sectional view of the second version of the suction control valve means 40 in its open position.

Figure 8D:
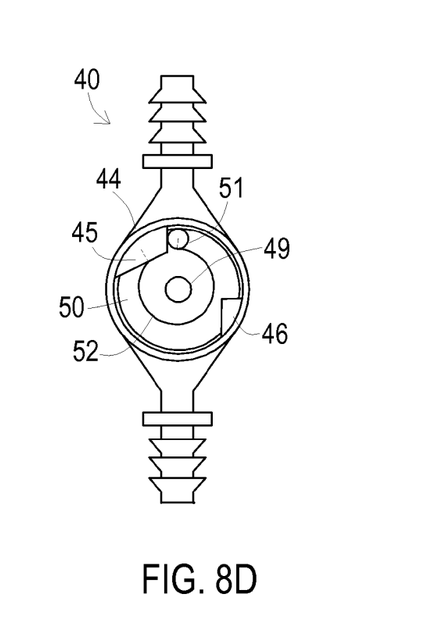
FIG. 8D is an end side cross-sectional view of the second version of the suction control valve means in its open position.

FIG. 8D illustrates a side view of the second version of the suction control valve means 40 without the side endplate and the knob where an operator has rotated the rotatable element 50 ninety degrees into its open activated position. The spring anchor block 45 also functions as a stop block and keeps the rotatable element from moving past its open position. The spring 52 is compressed and loaded in this position and it will force the rotatable element 50 back into its closed deactivated position when the operator releases the knob.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the disclosed technology and are intended to be covered by the following claims.

What is claimed is:

1. An endotracheal tube with intrinsic suction within and beyond as well as above-the-cuff suction outside the tube, the endotracheal tube comprising:
    an outer tube, the outer tube having a proximal end, a distal end, and a lumen, wherein the outer tube approximates an inner diameter of a body passage to be intubated;
    an inflatable cuff, encircling the outer tube near the distal end, and adapted to provide a seal;
    an intrinsic suction channel integrally formed within the lumen of the outer tube, the intrinsic suction channel spanning from above the proximal end to the distal end of the outer tube and having an opening at the distal end and a plurality of openings along a length of the intrinsic suction channel, the intrinsic suction channel configured to allow a plurality of fluids to be suctioned into the intrinsic suction channel from an area surrounding the distal end of the outer tube and from an area within the lumen of the outer tube; and
    an above-the-cuff suction channel integrally formed within the lumen of the outer tube, the above-the-cuff suction channel spanning from above the proximal end of the outer tube to immediately above the cuff and having a plurality of holes disposed immediately above the cuff and which open from the above-the-cuff suction channel to an outside of the outer tube at the above-the-cuff suction channel farthest distal extent and adapted to remove secretions which accumulate above the cuff within the trachea and outside of the outer tube.

2. The endotracheal tube of claim 1, further comprising:
    a suction select valve configured for operable selection between a first suction action in the intrinsic suction channel to remove secretions within the outer tube and beyond from the tracheobronchial system and a second suction action in the above-the-cuff suction channel to remove secretions above the cuff outside the outer tube and within the trachea;
    wherein either suction function is activated without the need to disconnect the gas delivery system.

3. The endotracheal tube of claim 1, further comprising:
    an endoscopy and medicine port configured for operable insertion of an endo scope and a medicine, wherein the endoscopy and medicine port is fluidly coupled to the intrinsic suction channel.

4. The endotracheal tube of claim 3, wherein the endoscopy and medicine port is adapted to directly administer medications into the tracheobronchial system without the need to uncouple and disconnect a gas delivery system and a suction system.

5. The endotracheal tube of claim 3, wherein the endoscopy and medicine port is adapted to receive the insertion of a flexible endoscope for videolaryngoscopy to assist in accurate passage of the endotracheal tube between the vocal cords and proper positioning with the trachea.

6. The endotracheal tube of claim 1, further comprising:
    a suction select valve configured for operable selection between a first suction action in the intrinsic suction channel to remove secretions within the outer tube and beyond from the tracheobronchial system and a second suction action in the above-the-cuff suction channel to remove secretions above the cuff outside the outer tube and within the trachea; and
    an endoscopy and medicine port configured for operable insertion of an endo scope and a medicine, wherein the endoscopy and medicine port is fluidly coupled to the intrinsic suction channel;
    wherein the intrinsic suction channel is defined by a Y-branch extended side arm, wherein a first branch of the Y is adapted for the suction select valve, and wherein a second branch of the Y is adapted for the endoscopy and medicine port.

7. The endotracheal tube of claim 1, further comprising:
    A suction extension tube having an opening defined at its terminus, fluidly coupled to the intrinsic suction channel and the above-the-cuff suction channel of the endotracheal tube and outwardly extending from generally the proximal end of the outer tube, to provide a removal path out of the body passage for the plurality of fluids suctioned into the intrinsic suction channel and the above-the-cuff suction channel.

8. The endotracheal tube of claim 7, further comprising:
    an end cap selectively placed on a proximal end of the suction extension tube to close the proximal end of the suction extension tube; and a security tether to connect the end cap to the suction extension tube;
    a locking plate extension having a locking plate opening defined in a margin of a body wall of the suction extension tube at the terminus and adjacent to the extension tube opening; and
    a cylindrical projection with a rounded tip defined with the end cap and adapted to securely couple to a tubular lumen of the suction extension tube when not in use.

9. The endotracheal tube of claim 7, further comprising:
    a suction select valve configured for operable selection between a first suction action in the intrinsic suction channel to remove secretions within the outer tube and beyond from the tracheobronchial system and a second suction action in the above-the-cuff suction channel to remove secretions above the cuff outside the outer tube and within the trachea, wherein the suction select valve is disposed with the suction extension tube.

10. The endotracheal tube of claim 1, wherein the intrinsic suction channel comprises a round circumferential shape, and wherein the plurality of openings along the length of the intrinsic suction channel are alternated from a first side to a second side of the intrinsic suction channel and staggered in distribution or otherwise.

11. The endotracheal tube of claim 1, further comprising:
an air passageway located within the wall of the outer tube and fluidly coupled to the inflatable cuff;
an inflation extension tube fluidly coupled to the air passageway in the wall of the outer tube and outwardly extending from the proximal end of the outer tube; and
a filler valve coupled to a proximal end of the inflation extension tube to regulate the flow of air entering or exiting the inflation extension tube and the inflatable cuff.

12. The endotracheal tube of claim 1, further comprising:
a radiopaque strip located within the outer tube in a portion of the outer tube located underneath the suction channel or elsewhere and extending longitudinally from the distal end of the outer tube to the proximate end of the outer tube to disallow the passage of radiation.

13. The endotracheal tube of claim 1, further comprising:
an opening in the side of the outer tube located between a tip of the endotracheal tube and an inflatable cuff to assist in ventilation and help avoid complete endotracheal tube obstruction.

14. The endotracheal tube of claim 2, wherein the suction select valve further comprises:
a valve housing;
a Y-shaped tubular passageway fluidly coupled to the intrinsic suction channel and the above-the-cuff suction channel, wherein a first branch of the Y is adapted for the intrinsic suction channel and wherein a second branch of the Y is adapted for the above-the-cuff suction channel; and
a cylindrical internal reciprocatable element adapted to rotate operably within the valve housing in a limited defined range between the first branch of the Y and the second branch of the Y, thereby between a first suction action in the intrinsic suction channel to remove secretions within the outer tube and beyond from the tracheobronchial system and a second suction action in the above-the-cuff suction channel to remove secretions above the cuff outside the outer tube and within the trachea.

15. A method for intubating a patient with an endotracheal tube having intrinsic suction and above-the-cuff suction, the method comprising:
providing an endotracheal tube comprising:
an outer tube, the outer tube having a proximal end, a distal end, and a lumen, wherein the outer tube approximates an inner diameter of a body passage to be intubated;
an inflatable cuff, encircling the outer tube near the distal end, and adapted to provide a seal;
an intrinsic suction channel integrally formed within the lumen of the outer tube, the intrinsic suction channel spanning from above the proximal end to the distal end of the outer tube and having an opening at the distal end and a plurality of openings along a length of the intrinsic suction channel, the intrinsic suction channel configured to allow a plurality of fluids to be suctioned into the intrinsic suction channel from an area surrounding the distal end of the outer tube and from an area within the lumen of the outer tube; and
an above-the-cuff suction channel integrally formed within the lumen of the outer tube, the above-the-cuff suction channel spanning from above the proximal end of the outer tube to immediately above the cuff and having a plurality of holes disposed immediately above the cuff and which open from the above-the-cuff suction channel to an outside of the outer tube at the above-the-cuff suction channel farthest distal extent and adapted to remove secretions which accumulate above the cuff within the trachea and outside of the outer tube;
placing the endotracheal tube within the patient; and
selectively utilizing the intrinsic suction channel as necessary to remove secretions within the outer tube and beyond from the tracheobronchial system;
selectively utilizing the above-the-cuff suction channel as necessary to remove secretions above the cuff outside the outer tube and within the trachea.

16. The method of claim 15, further comprising:
providing an endotracheal tube further comprising:
a suction select valve configured for operable selection between a first suction action in the intrinsic suction channel to remove secretions within the outer tube and beyond from the tracheobronchial system and a second suction action in the above-the-cuff suction channel to remove secretions above the cuff outside the outer tube and within the trachea; and
operatively turning the suction select valve to select the first suction action in the intrinsic suction channel and the second suction action in the above-the-cuff suction channel.

17. The method of claim 15, further comprising:
providing an endotracheal tube further comprising:
an endoscopy and medicine port configured for operable insertion of an endo scope and a medicine, wherein the endoscopy and medicine port is fluidly coupled to the intrinsic suction channel;
directly administering a medicine into the tracheobronchial system without the need to uncouple and disconnect a gas delivery system and a suction system; and
directly administering an insertion of a flexible endo scope for videolaryngoscopy to assist in accurate passage of the endotracheal tube between the vocal cords and proper positioning with the trachea.

18. The method of claim 15, further comprising:
providing an endotracheal tube further comprising:
a suction extension tube having an opening defined at its terminus, fluidly coupled to the intrinsic suction channel and the above-the-cuff suction channel of the endotracheal tube and outwardly extending from generally the proximal end of the outer tube, to provide a removal path out of the body passage for the plurality of fluids suctioned into the intrinsic suction channel and the above-the-cuff suction channel; and
removing the plurality of fluids suctioned into the intrinsic suction channel and the above-the-cuff suction channel.

19. The method of claim 15, further comprising:
providing an endotracheal tube further comprising:
an end cap selectively placed on a proximal end of the suction extension tube to close the proximal end of the extension tube;
a security tether to connect the end cap to the extension tube;
a locking plate extension having a locking plate opening defined in a margin of a body wall of the extension tube at the terminus and adjacent to the suction extension tube opening; and
a cylindrical projection with a rounded tip defined with the end cap and adapted to securely couple to a tubular lumen of the suction extension tube when not in use;

securely coupling the end cap to the tubular lumen of the suction extension tube when not in use; and
a like end cap with tether, locking plate and cylindrical projection securely coupling the end cap to the tubular lumen of the endoscopy/medicine port when not in use.

20. The method of claim 16, further comprising:
providing a suction select valve further comprising:
a valve housing;
a Y-shaped tubular passageway fluidly coupled to the intrinsic suction channel and the above-the-cuff suction channel, wherein a first branch of the Y is adapted for the intrinsic suction channel and wherein a second branch of the Y is adapted for the above-the-cuff suction channel; and
a cylindrical internal reciprocatable element adapted to rotate operably within the valve housing in a limited defined range between the first branch of the Y and the second branch of the Y, thereby between a first suction action in the intrinsic suction channel to remove secretions within the outer tube and beyond from the tracheobronchial system and a second suction action in the above-the-cuff suction channel to remove secretions above the cuff outside the outer tube and within the trachea; and
operatively selecting between the first suction action in the intrinsic suction channel and the second suction action in the above-the-cuff suction channel.

21. The method of claim 15, further comprising:
utilizing a valve configured to regulate a flow of the plurality fluids suctioned into the suction channel and out of the body passage, the valve having a fluid inlet port and a fluid outlet port configured for attachment to the extension tube and an external suction device.

22. The method of claim 15, further comprising:
providing a valve body; and
depressing a push-button coupled to the valve body to regulate an operation of the valve.

23. The method of claim 15, further comprising:
providing a valve body; and
rotating a rotatable turn-knob to turn a rotatable element disposed within the valve body, the rotatable turn-knob coupled to the rotatable element with a knob stem, to regulate an operation of the valve.

* * * * *